(12) United States Patent
Goldmann et al.

(10) Patent No.: US 6,255,330 B1
(45) Date of Patent: Jul. 3, 2001

(54) HETEROCYCLICALLY SUBSTITUTED PHENYLGLYCINOLAMIDES

(75) Inventors: Siegfried Goldmann; Ulrich Müller, both of Wuppertal (DE); Richard Connell, Trumbull, CT (US); Hilmar Bischoff; Dirk Denzer, both of Wuppertal (DE); Rudi Grützmann, Solingen (DE); Martin Beuck, Erkrath (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/553,202

(22) Filed: Apr. 20, 2000

Related U.S. Application Data

(62) Division of application No. 09/289,217, filed on Apr. 9, 1999, now abandoned, which is a division of application No. 08/835,914, filed on Apr. 10, 1997, now Pat. No. 5,935,984.

(30) Foreign Application Priority Data

Apr. 17, 1996 (DE) ............................................ 196 15 120
May 17, 1996 (DE) ............................................ 196 19 950

(51) Int. Cl.$^7$ ........................... A61K 31/427; A61P 9/10; C07D 277/14
(52) U.S. Cl. ........................... 514/369; 548/187; 548/188
(58) Field of Search ............................ 514/369; 548/187, 548/188

(56) References Cited

U.S. PATENT DOCUMENTS

| | | |
|---|---|---|
| 5,314,974 | 5/1994 | Ito et al. . |
| 5,352,687 | 10/1994 | Müller et al. . |
| 5,420,149 | 5/1995 | Müller et al. . |
| 5,521,206 | 5/1996 | Müller et al. . |
| 5,527,809 | 6/1996 | Müller-Gliemann et al. . |
| 5,576,342 | 11/1996 | Müller et al. . |

FOREIGN PATENT DOCUMENTS

| | | |
|---|---|---|
| 42 00 954 | 10/1992 | (DE) . |
| 43 01 900 | 7/1994 | (DE) . |
| 43 02 956 | 8/1994 | (DE) . |
| 43 09 968 | 9/1994 | (DE) . |
| 513 533 | 11/1992 | (EP) . |
| 542059 | 5/1993 | (EP) . |
| 560 162 | 9/1993 | (EP) . |
| 560 163 | 9/1993 | (EP) . |
| 565086 | 10/1993 | (EP) . |
| 565986 | 10/1993 | (EP) . |
| 610698 | 1/1994 | (EP) . |
| 608709 | 8/1994 | (EP) . |
| 622358 | 11/1994 | (EP) . |
| 624583 | 11/1994 | (EP) . |
| 630896 | 12/1994 | (EP) . |
| 705831 | 4/1996 | (EP) . |
| 716082 | 6/1996 | (EP) . |

*Primary Examiner*—Patricia L. Morris
(74) *Attorney, Agent, or Firm*—Norris McLaughlin & Marcus

(57) ABSTRACT

The heterocyclically substituted phenylglycinolamides are obtained by reaction of heterocyclically substituted phenylacetic acids with appropriate phenylglycinols. The heterocyclically substituted phenylglycinolamides are suitable as active compounds in medicaments, in particular in antiatherosclerotically active medicaments.

9 Claims, No Drawings

HETEROCYCLICALLY SUBSTITUTED PHENYLGLYCINOLAMIDES

This is a divisional of application Ser. No. 09/289,217, filed on Apr. 9, 1999, now abandoned which is a divisional of application Ser. No. 08/835,914, filed on Apr. 10, 1997, now U.S. Pat. No. 5,935,984.

The present invention relates to heterocyclically substituted phenylglycinolamides, processes for their preparation and their use as medicaments, in particular as antiatherosclerotic medicaments.

It is known that raised blood levels of triglycerides (hypertriglyceridaemia) and cholesterol (hypercholesterolaemia) are associated with the genesis of atherosclerotic vascular wad changes and coronary heart diseases.

A distinctly increased risk of the development of coronary heart diseases moreover exists if these two risk factors occur in combination, which in turn is accompanied by an overproduction of apoliprotein B-100. There is therefore still a great need to make available active medicaments for the control of atherosclerosis and coronary heart diseases.

The compounds according to the invention are partially covered by the widest scope of meaning of the publications DE 43 09 968, DE 43 02 956, DE 43 01 900, EP 565 086, EP 560 163, EP 560 162, EP 513 533 and DE 42 00 954, without a pharmacological representative of this type being mentioned there. The compounds mentioned here surprisingly show a decrease in or complete inhibition of the formation and/or the release of ApoB-100-associated lipoproteins from liver cells.

The present invention relates to heterocyclically substituted phenylglycinolamides of the general formula (I)

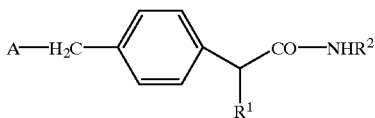

(I)

in which
A represents quinolyl or a radical of the formula

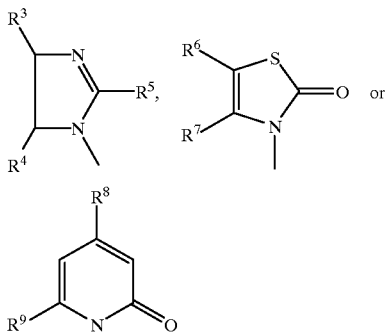

in which
$R^3$, $R^4$, $R^6$ and $R^7$ are identical or different and denote hydrogen, phenyl, halogen, formyl, carboxyl, straight-chain or branched alkoxycarbonyl having up to 4 carbon atoms or straight-chain or branched alkyl having up to 4 carbon atoms, which is optionally substituted by hydroxyl,
$R^5$ denotes phenyl, straight-chain or branched alkyl, acyl or alkylthio each having up to 6 carbon atoms or a group of the formula —CO—$NR^{10}R^{11}$, in which
$R^{10}$ and $R^{11}$ are identical or different and denote hydrogen or straight-chain or branched alkyl having up to 5 carbon atoms,
$R^8$ and $R^9$ are identical or different and denote hydrogen, straight-chain or branched alkyl or alkoxycarbonyl each having up to 6 carbon atoms or a radical of the formula —CO—$R^2$,
in which
$R^{12}$ denotes morpholinyl or the radical of the formula

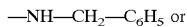

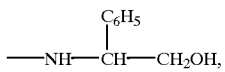

$R^1$ represents cycloalkyl having 3 to 8 carbon atoms, or represents straight-chain or branched alkyl having up to 10 carbon atoms,
$R^2$ represents a radical of the formula

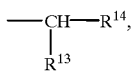

in which
$R^{13}$ denotes hydrogen or a radical of the formula $CH_2$—OH,
$R^{14}$ denotes phenyl which is optionally substituted up to 3 times identically or differently by hydroxyl, halogen or straight-chain or branched alkyl having up to 5 carbon atoms,
and their salts.

The heterocyclically substituted phenylglycinolamides according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers and to the diastereomers or their respective mixtures. These mixtures of the enantiomers and diastereomers can be separated in a known manner into the stereoisomerically uniform constituents.

Preferred compounds of the general formula (I) according to the invention are those
in which
A represents quinolyl or a radical of the formula

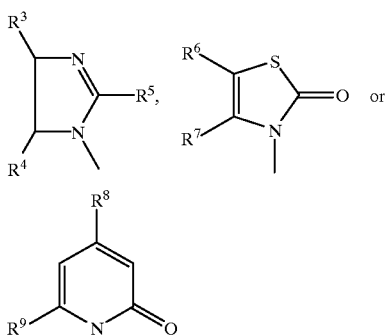

in which
R$^3$, R$^4$, R$^6$ and R$^7$ are identical or different and denote hydrogen, phenyl, fluorine, chlorine, bromine, formyl, straight-chain or branched alkoxycarbonyl having up to 3 carbon atoms or straight-chain or branched alkyl having up to 3 carbon atoms, which is optionally substituted by hydroxyl,
R$^5$ denotes phenyl, straight-chain or branched alkyl, acyl or alkylthio each having up to 5 carbon atoms or a group of the formula —CO—NR$^{10}$R$^{11}$,
in which
R$^{10}$ and R$^{11}$ are identical or different and denote hydrogen or straight-chain or branched alkyl having up to 5 carbon atoms,
R$^8$ and R$^9$ are identical or different and denote hydrogen, straight-chain or branched alkyl or alkoxycarbonyl each having up to 5 carbon atoms or a radical of the formula —CO—R$^{12}$,
in which
R$^{12}$ denotes morpholinyl or the radical of the formula

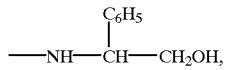

—NH—CH$_2$—C$_6$H$_5$ or

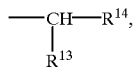

R$^1$ represents cyclopropyl, cyclobutyl, cyclopentyl, cyclohexyl or cycloheptyl, or represents straight-chain or branched alkyl having up to 8 carbon atoms,
R$^3$ represents a radical of the formula

—CH—R$^{14}$,
  |
  R$^{13}$ in which
R$^{13}$ denotes hydrogen or a radical of the formula CH$_2$—OH,
R$^{14}$ denotes phenyl which is optionally substituted up to 2 times identically or differently by hydroxyl, fluorine, chlorine, bromine or straight-chain or branched alkyl having up to 3 carbon atoms,
and their salts.

Particularly preferred compounds of the general formula (I) according to the invention are those in which A represents quinolyl or a radical of the formula

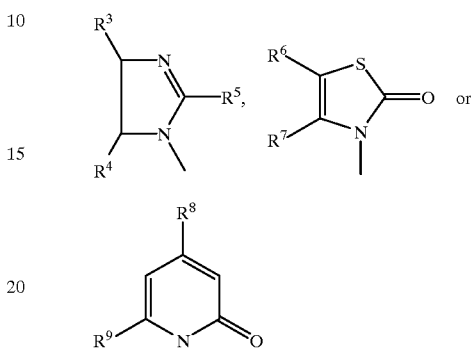

in which

R$^3$, R$^4$, R$^6$ and R$^7$ are identical or different and denote hydrogen, phenyl, chlorine, formyl, methoxycarbonyl, ethoxycarbonyl or methyl or ethyl, which is optionally substituted by hydroxyl, R$^5$ denotes phenyl, methylthio, acetyl, ethylthio or straight-chain or branched alkyl having up to 4 carbon atoms or a group of the formula —CO—NR$^{10}$R$^{11}$,
in which
R$^{10}$ and R$^{11}$ are identical or different and denote hydrogen or straight-chain or branched alkyl having up to 3 carbon atoms, R$^8$ denotes methyl, methoxycarbonyl, ethoxycarbonyl or the radical of the formula

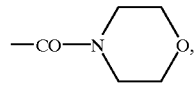

and

R$^9$ denotes hydrogen, methyl, propyl or butyl, and their salts.

Very particularly preferred compounds of the general formula (I) are those which are listed in the following table.

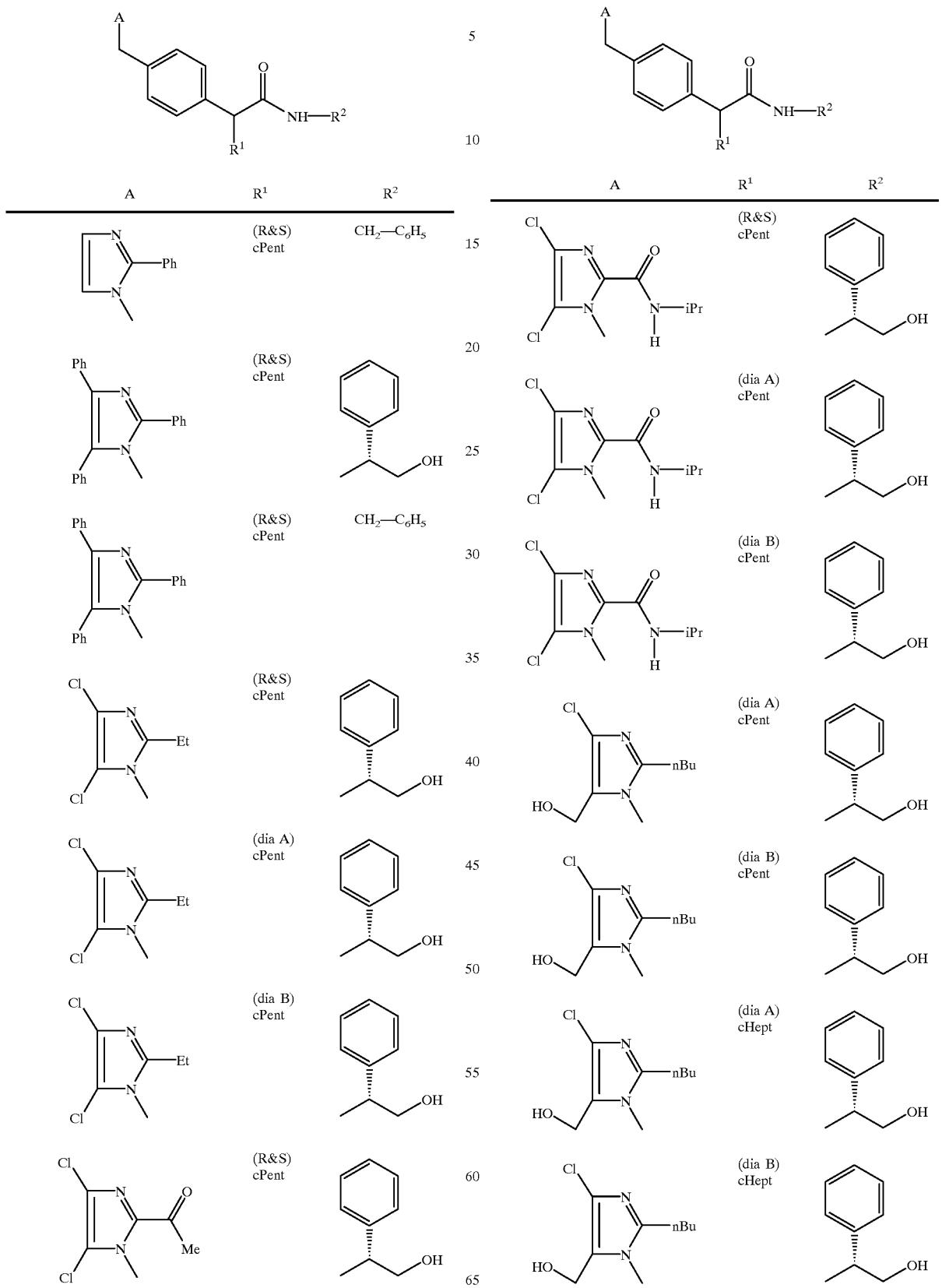

-continued
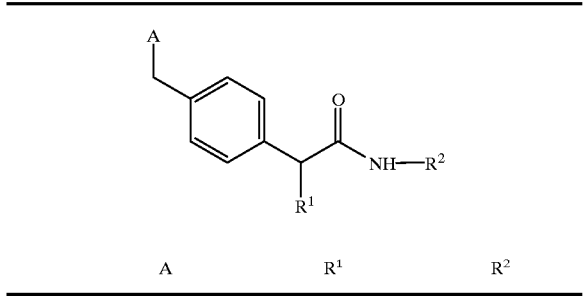
| A | R¹ | R² |
|---|---|---|
| 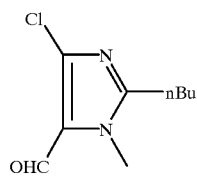 | (R&S) cPent | 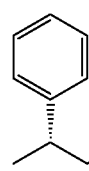 |
| 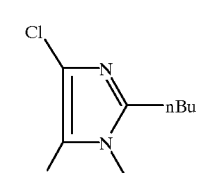 | (R&S) cHept | 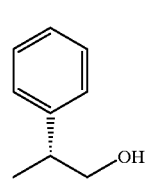 |
| 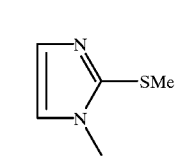 | (R&S) cPent | 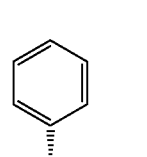 |
| 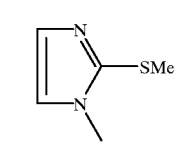 | (R&S) cPent | CH₂—C₆H₅ |
| 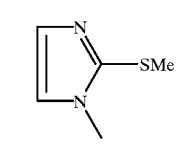 | (R&S) cPent | 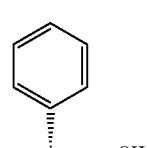 |
| 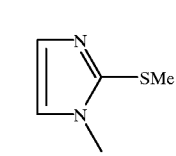 | (R&S) cHept | CH₂—C₆H₅ |
| 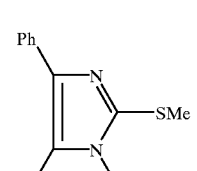 | (R&S) cPent | 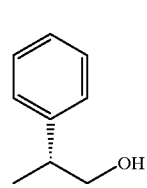 |
-continued
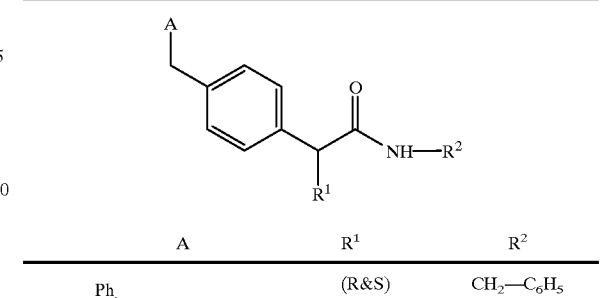
| A | R¹ | R² |
|---|---|---|
| 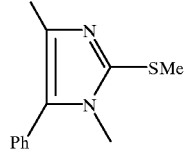 | (R&S) cPent | CH₂—C₆H₅ |
| 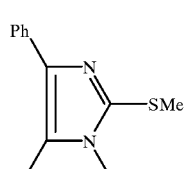 | (R&S) cHept | 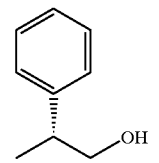 |
| 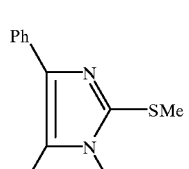 | (R&S) cHept | CH₂—C₆H₅ |
| 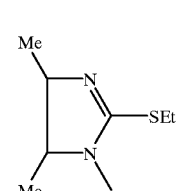 | (R&S) cPent | 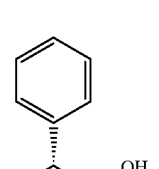 |
| 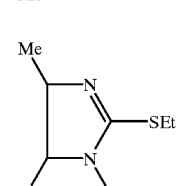 | (R&S) cPent | CH₂—C₆H₅ |
| 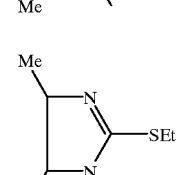 | (R&S) cHept | 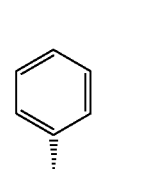 |
| 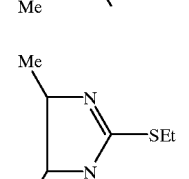 | (R&S) cHept | CH₂—C₆H₅ |

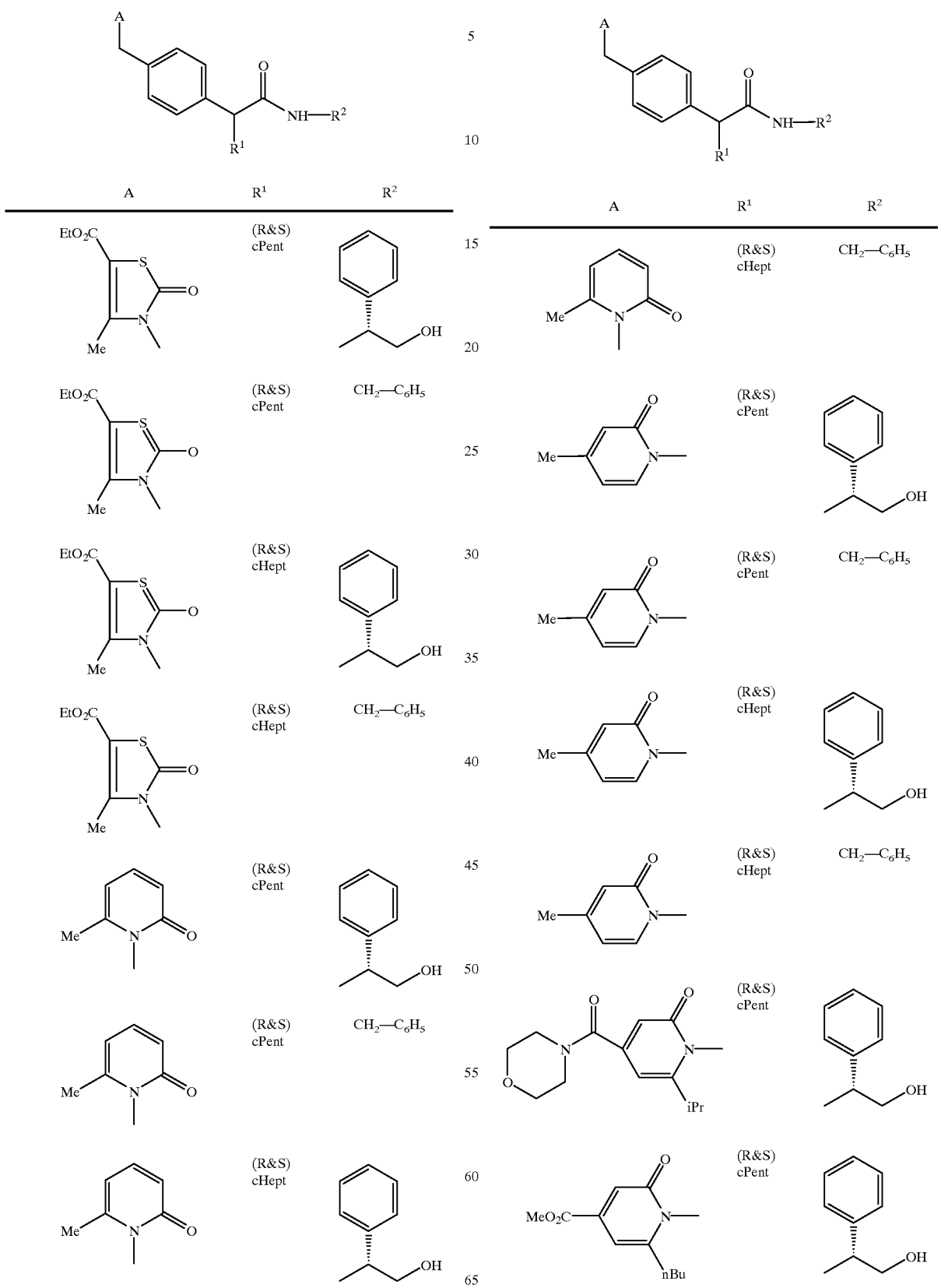

-continued

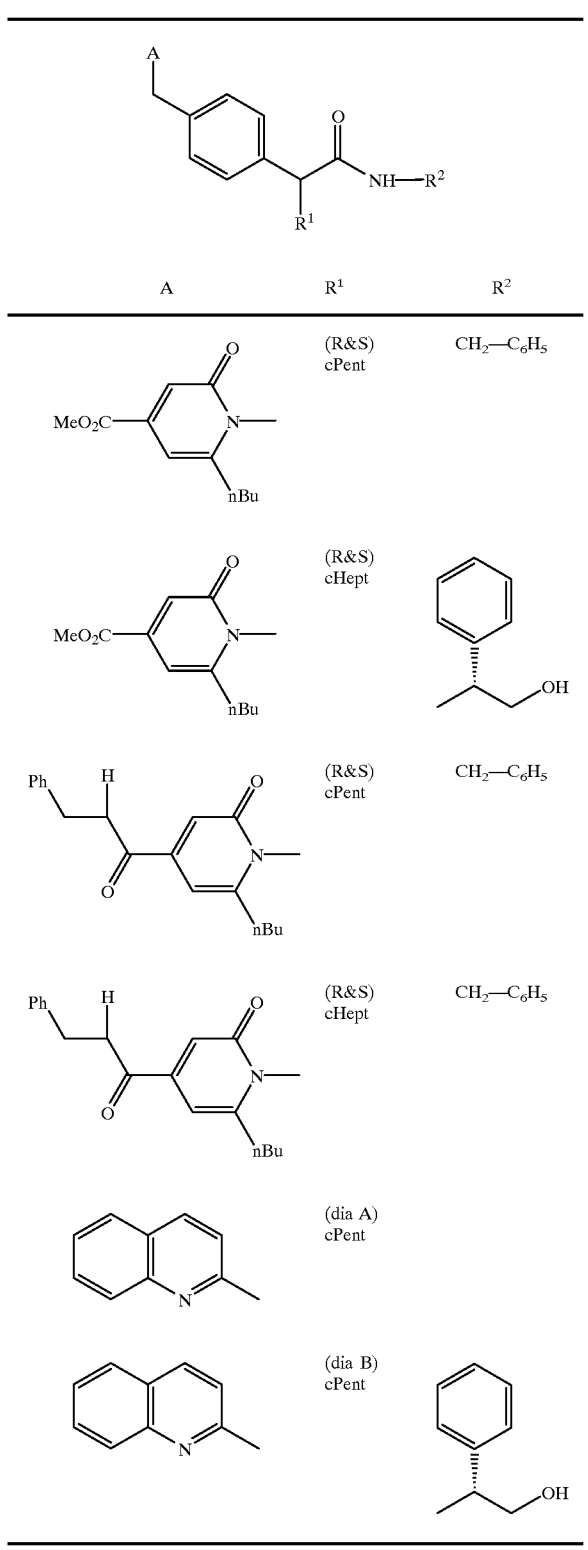

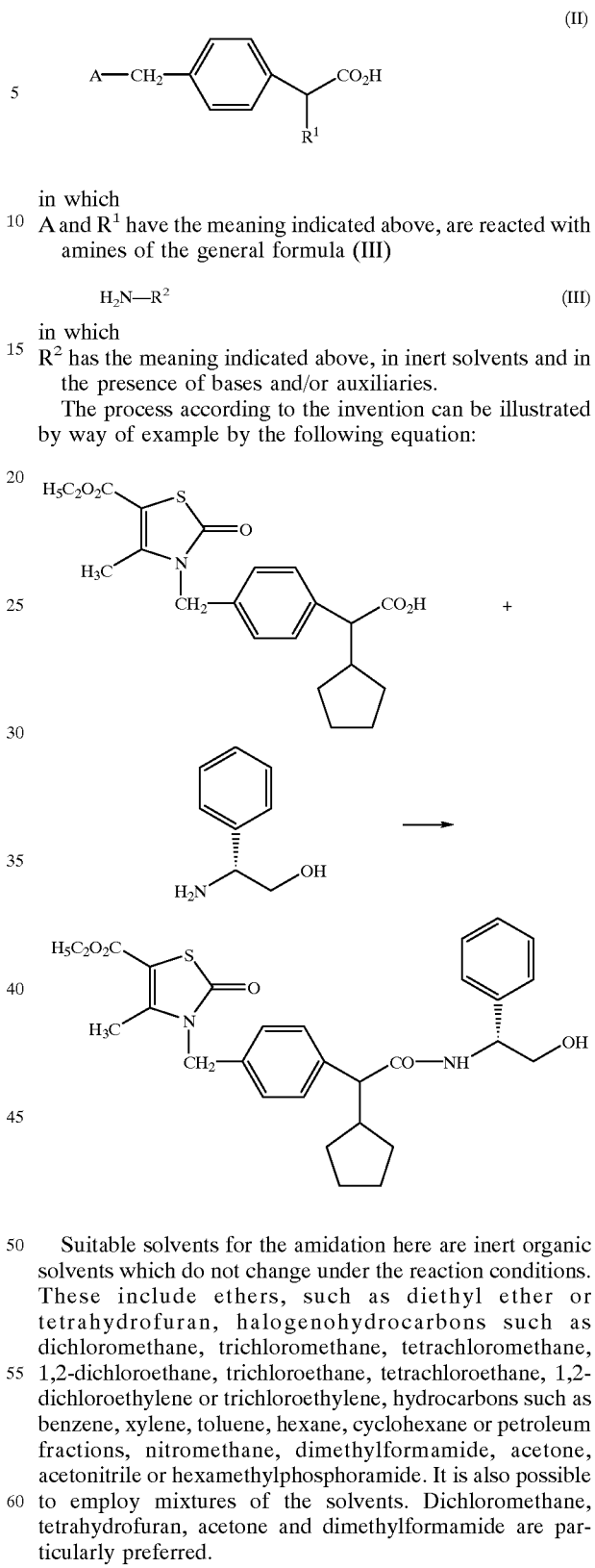

A process for the preparation of the compounds of the general formula (I) according to the invention has additionally been found, characterized in that carboxylic acids of the general formula (II)

in which
A and $R^1$ have the meaning indicated above, are reacted with amines of the general formula (III)

$$H_2N-R^2 \quad (III)$$

in which
$R^2$ has the meaning indicated above, in inert solvents and in the presence of bases and/or auxiliaries.

The process according to the invention can be illustrated by way of example by the following equation:

Suitable solvents for the amidation here are inert organic solvents which do not change under the reaction conditions. These include ethers, such as diethyl ether or tetrahydrofuran, halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or petroleum fractions, nitromethane, dimethylformamide, acetone, acetonitrile or hexamethylphosphoramide. It is also possible to employ mixtures of the solvents. Dichloromethane, tetrahydrofuran, acetone and dimethylformamide are particularly preferred.

In general, bases which can be employed for the process according to the invention are inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)amines) such as triethylamine or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals such as sodium and their hydrides such as sodium hydride. Sodium and potassium carbonate and triethylamine are preferred.

The base is employed in an amount from 1 mol to 5 mol, preferably from 1 mol to 3 mol. relative to 1 mol of the compound of the general formula (II).

The reaction is in general carried out in a temperature range from 0° C. to 150° C., preferably from +20° C. to +110° C.

The reaction can be carried out at normal, elevated or at reduced pressure (e.g. 0.5 to 5 bar). In general, it is carried out at normal pressure.

The amidation can optionally also proceed via the activated stage of the acid halides, which can be prepared from the corresponding acids by reaction with thionyl chloride, phosphorus trichloride, phosphorus pentachloride, phosphorus tribromide or oxalyl chloride.

The abovementioned bases can optionally also be employed as acid-binding auxiliaries for the amidation.

Suitable auxiliaries are also dehydrating reagents. These include, for example, carbodiimides such as diisopropylcarbodiimide, dicyclohexylcarbodiimide or N-(3-dimethylaminopropyl)-N'- ethylcarbodiimide hydrochloride or carbonyl compounds such as carbonyldiimidazole or 1,2-oxazolium compounds such as 2-ethyl-5-phenyl-1,2-oxazolium-3-sulph on ate or propanephosphonic anhydride or isobutyl chloroformate or benzotriazolyloxy-tris-(dimethylamino)-phosphonium hexafluorophosphate or diphenyl phosphoramidate or methane-sulphonyl chloride, if appropriate in the presence of bases such as triethylamine or N-ethylmorpholine or N-methylpiperidine, or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The variation of functional groups such as, for example, hydrolysis, esterification and reduction, as well as separation of isomers and salt formation are carried out by customary methods.

The carboxylic acids of the general formula (II) are in the main new and can be prepared by reacting compounds of the general formula (IV)

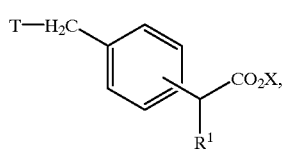

(IV)

in which

R$^1$ has the meaning indicated above,

T represents a typical leaving group such as, for example, chlorine, bromine, iodine, tosylate or mesylate, preferably bromine, and X represents ($C_1$–$C_4$)-alkyl, with compounds of the general formula (V)

$$A\text{—}H \quad (V)$$

in which

A has the meaning indicated in inert solvents, if appropriate in the presence of a base, and then hydrolysing the esters according to customary methods.

Suitable solvents for the process are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide and tetrahydrofuran are preferred.

In general, bases which can be employed for the process according to the invention are inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals such as sodium or their hydrides such as sodium hydride. Sodium hydride, potassium carbonate, triethylamine, pyridine and potassium tert-butoxide, DBU or DABCO are preferred.

In general, the base is employed in an amount from 0.05 mol to 10 mol, preferably from 1 mol to 2 mol, relative to 1 mol of the compound of the formula (IV).

The process according to the invention is in general carried out in a temperature range from –30° C. to +100° C., preferably from –10° C. to +60° C.

The process according to the invention is in general carried out at normal pressure. However, it is also possible to carry out the process at elevated pressure or at reduced pressure (e.g. in a range from 0.5 to 5 bar).

The compounds of the general formula (III) are known per se.

The compounds of the general formula (IV) are known or can be prepared in analogy to known methods.

The compounds of the general formula (V) are known or can be prepared in analogy to known methods.

The compounds of the general formula (I) according to the invention have an unforeseeable spectrum of pharmacological action.

They can be used as active compounds in medicaments for the reduction of changes to vascular walls and for the treatment of coronary heart diseases, cardiac insufficiency, brain function disorders, ischaemic cerebral disorders, apoplexy, circulatory disorders, disorders of the microcirculation and thromboses.

The proliferation of smooth muscle cells furthermore plays a decisive part in the occlusion of vessels. The compounds according to the invention are suitable for inhibiting this proliferation and thus preventing atherosclerotic processes.

The compounds according to the invention are distinguished by a lowering of the ApoB-100-associated lipoproteins (VLDL and its degradation products, such as, for example, LDL), of ApoB-100, of triglycerides and of cholesterol. They thus have useful pharmacological properties which are superior compared with the prior art.

Surprisingly, the action of the compounds according to the invention consists first in a decrease in or complete inhibition of the formation and/or the release of ApoB-100-associated lipoproteins from liver cells, which results in a lowering of the VLDL plasma level. This lowering of VLDL has to be accompanied by a lowering of the plasma levels of ApoB-100, LDL, triglycerides and of cholesterol; thus simultaneously several of the abovementioned risk factors which are involved in vascular wall changes are lowered.

The compounds according to the invention can therefore be employed for the prevention and treatment of atherosclerosis, obesity, pancreatitis and constipation.

1. Inhibition of the Release of ApoB-100-associated Lipoproteins

The test for detecting the inhibition of the release of ApoB-100-associated lipoproteins from liver cells was carried out in vitro using cultured liver cells, preferably using cells of the human line HepG2. These cells were cultured under standard conditions in medium for the culture of eukaryotic cells, preferably in RPMI 1640 using 10% foetal calf serum. HepG2 cells synthesize and secrete into the culture supernatant ApoB-100-associated lipoprotein particles which in principle are built up in a similar manner to the VLDL and LDL particles which are to be found in the plasma.

These particles can be detected using an immunoassay for human LDL. This immunoassay is carried out using antibodies which have been induced under standard conditions against human LDL in rabbits. The anti-LDL antibodies (rabbit anti-LDL ABs) were purified by affinity chromatography on an immunosorbent using human LDL. These purified rabbit anti-LDL ABs are adsorbed on the surface of plastic. Expediently, this adsorption is carried out on the plastic surface of microtitre plates having 96 wells, preferably on MaxiSorp plates. If ApoB-100-associated particles are present in the supernatant of Hep-G2 cells, then these can bind to the insolubilized rabbit anti-LDL ABs, and an immune complex results which is bound to the plastic surface. Non-bound proteins are removed by washing. The immune complex situated on the plastic surface is detected using monoclonal antibodies Rich have been induced against human LDL and purified under standard conditions. These antibodies were conjugated with the enzyme peroxidase. Peroxidase converts the colourless substrate TMB into a coloured product in the presence of $H_2O_2$. After acidification of the reaction mixture with $H_2SO_4$, the specific light adsorption at 450 nm is determined, which is a measure of the amount of ApoB-100-associated particles which has been secreted into the culture supernatant by the HepG2 cells.

Surprisingly, the compounds according to the invention inhibit the release of ApoB-100-associated particles. The $IC_{50}$ indicates at which substance concentration the light adsorption is inhibited by 50% in comparison to the control (solvent control without substance).

2. Determination of VLDL Secretion in vivo in the Hamster

The effect of the test substances on VLDL secretion in vivo is investigated in the hamster. To do this, golden hamsters are anaesthetized with Ketavet (83 mg/kg s.c.) and Nembutal (50 mg/kg i.p.) after premedication with atropine (83 mg/kg s.c.). When the animals have become reflex-free, the jugular vein is exposed and cannulated. 0.25 ml/kg of a 20% strength solution of Triton WR-1339 in physiological saline solution is then administered. This detergent inhibits the lipoprotein lipase and thus leads to a rise in the triglyceride level on account of an absent catabolism of secreted VLDL particles. This triglyceride rise can be used as a measure of the VLDL secretion rate. Blood is taken from the animals before and one and two hours after administration of the detergent by puncture of the retroorbital venous plexus. The blood is incubated for two hours at room temperature, then overnight at 4° C. in order to finish clotting completely. It is then centrifuged at 10,000 g for 5 minutes. In the serum thus obtained, the triglyceride concentration is determined with the aid of a modified commercially available enzyme test (Merckotest® triglyceride No. 14354). 100 µl of serum are treated with 100 µl of test reagent in 96-hole plates and incubated at room temperature for 10 minutes. The optical density is then determined at a wavelength of 492 nm in an automatic plate-reading apparatus (SLT spectra). Serum samples having too high a triglyceride concentration are diluted with physiological saline solution. The triglyceride concentration contained in the samples is determined with the aid of a standard curve measured in parallel. In this model, test substances are administered intravenously either immediately before administration of the detergent or orally or subcutaneously before initiation of anaesthesia.

3. Inhibition of Intestinal Triglyceride Absorption in vivo (Rats)

The substances which are to be investigated for their triglyceride absorption-inhibiting action in vivo are administered orally to male Wistar rats having a body weight of between 170 and 230 g. For this purpose, the animals are divided into groups of 6 animals 18 hours before administration of substance and the feed is then withdrawn from them. Drinking water is available to the animals ad libitum. The animals of the control groups receive an aqueous tragacanth suspension or a tragacanth suspension which contains olive oil. The tragacanth-olive oil suspension is prepared using the Ultra-Turrax. The substances to be investigated are suspended in an appropriate tragacanth-olive oil suspension, likewise using the Ultra-Turrax, directly before substance administration.

Blood is taken from each rat by puncture of the retroorbital venous plexus before stomach tube application to determine the basal serum triglyceride content. The tragacanth suspension, the tragacanth-olive oil suspensions without substance (control animals), or the substances suspended in an appropriate tragacanth-olive oil suspension are then administered to the fasting animals using a stomach tube. Further taking of blood to determine the postprandial serum triglyceride rise is generally carried out 1, 2 and 3 hours after stomach tube application.

The blood samples are centrifuged and, after recovering the serum, the triglycerides are determined photometrically using an EPOS analyser 5060 (Eppendorf Geräitebau, Netheler & Hinz GmbH, Hamburg). The determination of the triglycerides is carried out completely enzymatically using a commercially available UV test.

The postprandial serum triglyceride rise is determined by subtraction of the triglyceride preliminary value of each animal from its corresponding postprandial triglyceride concentrations (1, 2 and 3 hours after administration).

The differences (in mmol/l) at each time (1, 2 and 3 hours) are averaged in the groups, and the average values of the serum triglyceride rise (ATG) of the substance-treated animals are compared with the animals which only received the tragacanth-oil suspension.

The serum triglyceride course of the control animals which only received tragacanth is likewise calculated. The substance effect at each time (1, 2 or 3 hours) is determined as follows and indicated in Δ% of the oil-loaded control.

$$\Delta\% \text{ triglyceride rise} = \frac{\Delta TG_{substance} - \Delta TG_{tragacanth\ control}}{\Delta TG_{oil\ loading} - \Delta TG_{tragacanth\ control}} \times 100$$

Effect of 10 mg of test substance/kg of body weight p.o. on the triglyceride rise (Δ%) 2 h after a triglyceride loading in the serum of fasting rats. The serum triglyceride rise of fat-loaded control animals relative to the serum triglyceride level of tragacanth control animals corresponds to 100%. n=6 animals per group.

Statistical analysis is carried out using Student's t-test after prior checking of the variances for homogeneity.

Substances which at one time statistically significantly (p<0.05) decrease the postprandial serum triglyceride rise by at least 30%, compared with the untreated control group, are regarded as pharmacologically active.

4. Inhibition of VLDL Secretion in vivo (Rat)

The action of the test substances on VLDL secretion is likewise investigated in the rat. To do this, Triton WR-1339 (2.5 mg/kg), dissolved in physiological saline solution, is administered intravenously into the tail vein of rats of 500 mg/kg body weight. Triton WR-1339 inhibits lipoprotein lipase and thus leads by inhibition of VLDL catabolism to a rise in the triglyceride and cholesterol level. These rises can be used as a measure of the VLDL secretion rate.

Blood is taken from the animals by puncture of the retroorbital venous plexus before and one and two hours after administration of the detergent. The blood is incubated at room temperature for 1 h for clothing and the serum is recovered by centrifugation at 10,000 g for 20 s. The triglycerides are then determined photometrically at a wavelength of 540 nm by means of a commercially available coupled enzyme test (Sigma Diagnostics®, No. 339). Measurement is carried out with the aid of a likewise coupled enzyme test (Boehringer Mannheim®, No. 1442350) at a wavelength of 546 nm. Samples having triglyceride or cholesterol concentrations which exceed the measuring range of the methods are diluted with physiological saline solution. The determination of the respective serum concentrations is carried out with the aid of standard series measured in parallel. Test substances are administered orally, intravenously or subcutaneously immediately after Triton injection.

The invention additionally relates to the combination of heterocyclically substituted phenylglycinolamides of the general formula (I) with a glucosidase and/or amylase inhibitor for the treatment of familiar hyperlipidaemias, of obesity (adiposity) and of diabetes mellitus. Glucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, it being possible, for example, if water is used as a diluent optionally to use organic solvents as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proved advantageous in the case of intravenous administration to administer amounts of approximately 0.001 to 1 mg/kg, preferably approximately 0.01 to 0.5 mg/kg, of body weight to achieve effective results, and in the case of oral administration the dose is approximately 0.01 to 20 mg/kg, preferably 0.1 to 10 mg/kg, of body weight.

In spite of this, it may, if appropriate, be necessary to depart from the amounts mentioned, namely depending on the body weight or on the type of administration route, on individual behaviour towards the medicament, the manner of its formulation and the time or interval at which administration takes place. Thus, in some cases it may be adequate to manage with less than the abovementioned minimum amount, while in other cases the upper limit mentioned has to be exceeded. In the case of the administration of larger amounts, it may be advisable to divide these into several individual doses over the course of the day.

Abbreviations Used:
Ph=phenyl
Me=methyl
Et=ethyl
cHex=cyclohexyl
Bn=CH$_2$—C$_6$H$_5$

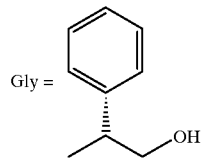

C=cyclohexane
EA=ethyl acetate
P=petroleum ether
Starting Compounds

EXAMPLE I tert-Butyl 2- cyclopentyl-2-[4-(2-phenyl- imidazol-1-yl-methyl)phenyl]acetate

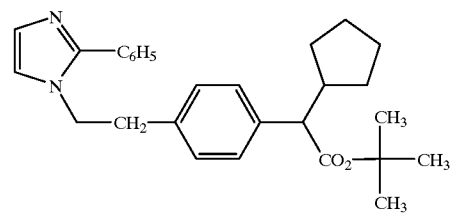

1.44 g (10 mmol) of 2-phenylimidazole are dissolved in 10 ml of DMF, deprotonated (50° C.) using 330 mg (11 mmol) of NaH (80% strength) and the solution is then treated with 3.5 g (10 mmol) of tert-butyl 4-bromomethyl-2-cyclopentyl-acetate (DE 42 00 954 A1) and stirred overnight at RT. It is concentrated, the residue is dissolved in $CH_2Cl_2$, the solution is washed with $H_2O$ and concentrated and the residue is chromatographed on silica gel (cyclohexane/EA=8:2).

3.2 g (75%) are obtained as a colourless resin.

EXAMPLE II

2-Cyclopentyl-2- [4-(2-phenyl- imidazol-1-yl-methyl) phenyl]acetic acid

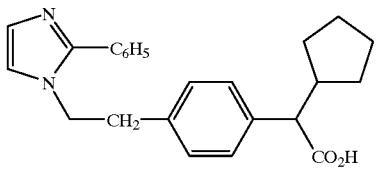

3.0 g (7 mmol) of the compound from Example I are dissolved in 14 ml of dioxane, treated with 2 ml of conc. HCl and the solution is refluxed for 5 h. It is concentrated, the residue is taken up in $CH_2Cl_2$ and the solution is washed with water. 2.6 g (96%) of the title compound are obtained as an oil.

The examples listed in Table I are prepared in analogy to the procedure of Example II.

TABLE I

| Ex. No. | A | $R^1$ | M.p. (° C.) | $R_f$ |
|---|---|---|---|---|
| III | (2-Ph-imidazol-1-yl)methyl | (R&S) cPent | 224 | |
| IV | (2,4,5-triphenyl-imidazol-1-yl)methyl | (R&S) cPent | 194 | |
| V | (4,5-dichloro-2-ethyl-imidazol-1-yl)methyl | (R&S) cPent | | |
| VI | (4,5-dichloro-2-acetyl-imidazol-1-yl)methyl | (R&S) cPent | | 0.48 C/EA 1:1 |
| VII | (4,5-dichloro-2-(N-isopropylcarbamoyl)-imidazol-1-yl)methyl | (R&S) cPent | | |

TABLE I-continued

| Ex. No. | A | R¹ | M.p. (° C.) | R$_f$ |
|---|---|---|---|---|
| VIII | 4-chloro-5-(hydroxymethyl)-2-nBu-1-Me-imidazole | (dia A) cPent | | |
| IX | 4-chloro-5-formyl-2-nBu-1-Me-imidazole | (R&S) cPent | | |
| X | 2-SMe-1-Me-imidazole | (R&S) cPent | 172 | |
| XI | 2-SMe-1-Me-imidazole | (R&S) cHept | 177 | |
| XII | 4,5-diPh-2-SMe-1-Me-imidazole | (R&S) cPent | | 0.2 C/EA 1:1 |
| XIII | 4,5-diPh-2-SMe-1-Me-imidazole | (R&S) cHept | 206 | |
| XIV | 4,5-diMe-2-SEt-1-Me-imidazoline | (R&S) cPent | | 0.17 CH$_2$Cl$_2$/MeOH H 9:1 |

TABLE I-continued

![Structure: A-CH2-C6H4-CH(R1)-COOH]

| Ex. No. | A | R¹ | M.p. (° C.) | R_f |
|---|---|---|---|---|
| XV | 1,4,5-trimethyl-2-(ethylthio)-4,5-dihydroimidazole | (R&S) cHept | | 0.25 CH₂Cl₂/MeOH 9:1 |
| XVI | ethyl 3,4-dimethyl-2-oxo-2,3-dihydrothiazole-5-carboxylate | (R&S) cPent | | 0.3 C/EA 1:1 |
| XVII | ethyl 3,4-dimethyl-2-oxo-2,3-dihydrothiazole-5-carboxylate | (R&S) cHept | | 0.32 C/EA 1:1 |
| XVIII | 1,6-dimethyl-2(1H)-pyridinone | (R&S) cPent | 203 | |
| XIX | 1,6-dimethyl-2(1H)-pyridinone | (R&S) cHept | 192 | |
| XX | 1,4-dimethyl-2(1H)-pyridinone | (R&S) cPent | 156 | |
| XXI | 1,4-dimethyl-2(1H)-pyridinone | (R&S) cHept | 200 | |

TABLE I-continued

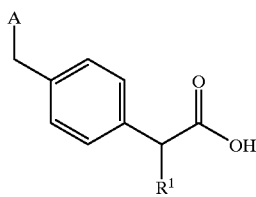

| Ex. No. | A | R¹ | M.p. (° C.) | $R_f$ |
|---|---|---|---|---|
| XXII | morpholine-C(O)- attached to 1-methyl-6-iPr-2-oxo-1,2-dihydropyridin-4-yl | (R&S) cPent | | 0.45 CH₂Cl₂/MeOH 9:1 |
| XXIII | MeO₂C- attached to 1-methyl-6-nBu-2-oxo-1,2-dihydropyridin-4-yl | (R&S) cPent | | |
| XXIV | MeO₂C- attached to 1-methyl-6-nBu-2-oxo-1,2-dihydropyridin-4-yl | (R&S) cHept | | |
| XXV | PhCH₂NHC(O)- attached to 1-methyl-6-nBu-2-oxo-1,2-dihydropyridin-4-yl | (R&S) cPent | | |
| XXVI | 2-methylquinolin-3-yl | (dia A) cPent | | |
| XXVII | 2-methylquinolin-3-yl | (dia B) cPent | | |

PREPARATION EXAMPLES

EXAMPLE 1

2-Cyclopentyl-N-(2-hydroxy-1-(R)-phenylethyl)-2-[4-(2-phenylimidazol-1-yl-methyl)phenyl]acetamide

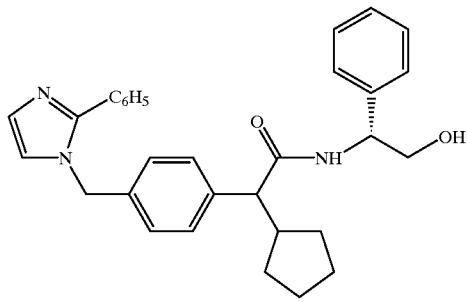

1.08 g (3 mmol) of the compound from Example II are dissolved in 30 ml of $CH_2Cl_2$ with 0.412 g (3 mmol) of R-(−)-2-phenylglycinol (Aldrich), then 0.446 g (3.3 mmol) of 1-hydroxy-1H-benzotriazole hydrate (Aldrich) are added. After addition of 662 mg (3.45 mmol) of N'-(3-dimethylaminopropyl)-N-ethylcarbodiimide hydrochloride (Aldrich) and 0.8 ml of triethylamine, the mixture is stirred at RT overnight. It is diluted with $CH_2Cl_2$, washed once each with $NH_4Cl$ solution and $NaHCO_3$ solution, dried and concentrated in a rotary evaporator. The residue is chromatographed using cyclohexane/ethyl acetate (1:1).

Yield: 1.46 g (98%).

$R_f$=0.17 (cyclohexane/ethyl acetate=1:1)

The compounds listed in Table 1 are prepared via the corresponding precursors (analogously to Examples I and II) in analogy to the procedure of Example 1:

TABLE 1

| Ex. No. | A | $R^1$ | $R^2$ | M.p. (° C.) | $R_f$ |
|---|---|---|---|---|---|
| 2 | 2-Ph-imidazol-1-ylmethyl | (R&S) cPent | N-Bn | | 0.12 C/EA 4:6 |
| 3 | 4,5-diPh-2-Ph-imidazol-1-ylmethyl | (R&S) cPent | R-Gly | 175 | |
| 4 | 4,5-diPh-2-Ph-imidazol-1-ylmethyl | (R&S) cPent | Bn | | 0.25 C/EA 7:3 |
| 5 | 4,5-diCl-2-Et-imidazol-1-ylmethyl | (R&S) cPent | R-Gly | | 0.5 $CH_2Cl_2/CH_3OH$ 10:1 |

TABLE 1-continued

| Ex. No. | A | R¹ | R² | M.p. (° C.) | $R_f$ |
|---|---|---|---|---|---|
| 6 | 4,5-dichloro-2-ethyl-1-methyl-imidazole | (dia A) cPent | R-Gly | | 0.5 CH₂Cl₂/CH₃OH 10:1 |
| 7 | 4,5-dichloro-2-ethyl-1-methyl-imidazole | (dia B) cPent | R-Gly | | 0.5 CH₂Cl₂/CH₃OH 10:1 |
| 8 | 4,5-dichloro-2-acetyl-1-methyl-imidazole | (R&S) cPent | R-Gly | 154 | |
| 9 | 4,5-dichloro-1-methyl-imidazole-2-carboxamide N-iPr | (R&S) cPent | R-Gly | | 0.39 P/EA 1:1 |
| 10 | 4,5-dichloro-1-methyl-imidazole-2-carboxamide N-iPr | (dia A) cPent | R-Gly | | 0.43 P/EA 1:1 |
| 11 | 4,5-dichloro-1-methyl-imidazole-2-carboxamide N-iPr | (dia B) cPent | R-Gly | | 0.35 P/EA 1:1 |
| 12 | 4-chloro-2-nBu-5-hydroxymethyl-1-methyl-imidazole | (dia A) cPent | R-Gly | | 0.16 P/EA 4:6 |

TABLE 1-continued
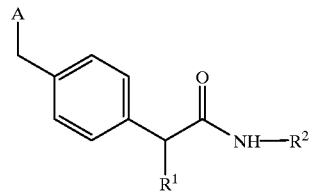
| Ex. No. | A | R¹ | R² | M.p. (° C.) | Rf |
|---|---|---|---|---|---|
| 13 | 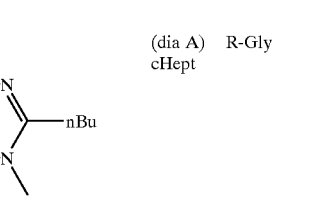 | (dia B) cPent | R-Gly | | 0.09 P/EA 4:6 |
| 14 | 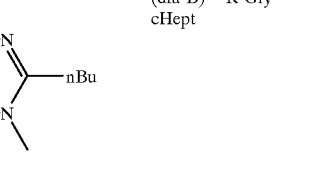 | (dia A) cHept | R-Gly | | 0.24 P/EA 4:6 |
| 15 | 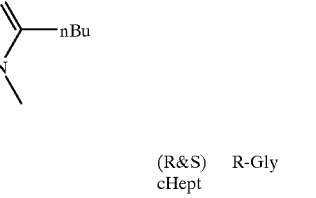 | (dia B) cHept | R-Gly | | 0.12 P/EA 4:6 |
| 16 | 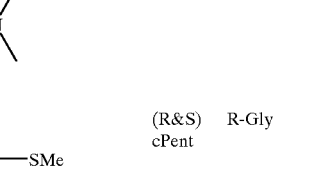 | (R&S) cPent | R-Gly | | 0.35 P/EA 1:1 |
| 17 | 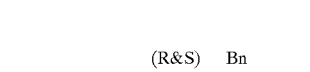 | (R&S) cHept | R-Gly | | 0.44 P/EA 1:1 |
| 18 |  | (R&S) cPent | R-Gly | | 0.58 C/EA 4:6 |
| 19 |  | (R&S) cPent | Bn | 105–106 | |

TABLE 1-continued

| Ex. No. | A | R¹ | R² | M.p. (° C.) | $R_f$ |
|---|---|---|---|---|---|
| 20 | 1-methyl-2-(methylthio)imidazol-4-yl | (R&S) cHept | R-Gly | | 0.08 C/EA 4:6 |
| 21 | 1-methyl-2-(methylthio)imidazol-4-yl | (R&S) cHept | Bn | | 0.2 C/EA 4:6 |
| 22 | 4,5-diphenyl-1-methyl-2-(methylthio)imidazol-yl | (R&S) cPent | R-Gly | | 0.28 C/EA 1:1 |
| 23 | 4,5-diphenyl-1-methyl-2-(methylthio)imidazol-yl | (R&S) cPent | Bn | 119–120 | |
| 24 | 4,5-diphenyl-1-methyl-2-(methylthio)imidazol-yl | (R&S) cHept | R-Gly | | 0.32 C/EA 1:1 |
| 25 | 4,5-diphenyl-1-methyl-2-(methylthio)imidazol-yl | (R&S) cHept | Bn | 168–169 | |
| 26 | 4,5-dimethyl-1-methyl-2-(ethylthio)imidazolin-yl | (R&S) cPent | R-Gly | | 0.11 CH$_2$Cl$_2$/CH$_3$OH 9:1 |

TABLE 1-continued

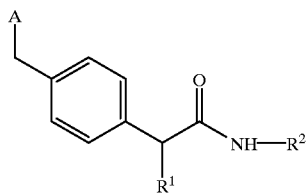

| Ex. No. | A | R[1] | R[2] | M.p. (° C.) | $R_f$ |
|---|---|---|---|---|---|
| 27 | Me, Me-substituted imidazoline with SEt and N-Me | (R&S) cPent | Bn | | 0.25 CH$_2$Cl$_2$/CH$_3$OH 9:1 |
| 28 | Me, Me-substituted imidazoline with SEt and N-Me | (R&S) cHept | R-Gly | | 0.23 CH$_2$Cl$_2$/CH$_3$OH 9:1 |
| 29 | Me, Me-substituted imidazoline with SEt and N-Me | (R&S) cHept | Bn | | 0.19 CH$_2$Cl$_2$/CH$_3$OH 9:1 |
| 30 | EtO$_2$C-, Me-substituted thiazolone | (R&S) cPent | R-Gly | | 0.18 C/EA 1:1 |
| 31 | EtO$_2$C-, Me-substituted thiazolone | (R&S) cPent | Bn | | 0.15 C/EA 7:3 |
| 32 | EtO$_2$C-, Me-substituted thiazolone | (R&S) cHept | R-Gly | | 0.21 C/EA 1:1 |
| 33 | EtO$_2$C-, Me-substituted thiazolone | (R&S) cHept | Bn | | 0.22 C/EA 7:3 |

TABLE 1-continued

| Ex. No. | A | R¹ | R² | M.p. (° C.) | $R_f$ |
|---|---|---|---|---|---|
| 34 | 6-Me-1-Me-pyridin-2(1H)-one | (R&S) cPent | R-Gly | | 0.27 CH₂Cl₂/CH₃OH 95:5 |
| 35 | 6-Me-1-Me-pyridin-2(1H)-one | (R&S) cPent | Bn | 173–174 | |
| 36 | 6-Me-1-Me-pyridin-2(1H)-one | (R&S) cHept | R-Gly | | 0.25 CH₂Cl₂/CH₃OH 95:5 |
| 37 | 6-Me-1-Me-pyridin-2(1H)-one | (R&S) cHept | Bn | 175–176 | |
| 38 | 4-Me-1-Me-pyridin-2(1H)-one | (R&S) cPent | R-Gly | | 0.28 CH₂Cl₂/CH₃OH 95:5 |
| 39 | 4-Me-1-Me-pyridin-2(1H)-one | (R&S) cPent | Bn | 146 | |
| 40 | 4-Me-1-Me-pyridin-2(1H)-one | (R&S) cHept | R-Gly | | 0.03 CH₂Cl₂/CH₃OH 95:5 |
| 41 | 4-Me-1-Me-pyridin-2(1H)-one | (R&S) cHept | Bn | 186 | |

TABLE 1-continued

[Structure: para-substituted benzene with CH2-A group and CHR1-C(=O)-NH-R2 side chain]

| Ex. No. | A | R¹ | R² | M.p. (° C.) | R_f |
|---|---|---|---|---|---|
| 42 | 4-(morpholine-4-carbonyl)-1-methyl-6-iPr-2-oxo-1,2-dihydropyridine | (R&S) cPent | R-Gly | | 0.31 CH₂Cl₂/CH₃OH 95:5 |
| 43 | 4-MeO₂C-1-methyl-6-nBu-2-oxo-1,2-dihydropyridine | (R&S) cPent | R-Gly | | 0.3 CH₂Cl₂/CH₃OH 95:5 |
| 44 | 4-MeO₂C-1-methyl-6-nBu-2-oxo-1,2-dihydropyridine | (R&S) cPent | Bn | | 0.4 C/EA 4:6 |
| 45 | 4-MeO₂C-1-methyl-6-nBu-2-oxo-1,2-dihydropyridine | (R&S) cHept | R-Gly | | 0.2 CH₂Cl₂/CH₃OH 95:5 |
| 46 | 4-(PhCH₂NHC(O))-1-methyl-6-nBu-2-oxo-1,2-dihydropyridine | (R&S) cPent | Bn | | 0.21 C/EA 4:6 |
| 47 | 4-(PhCH₂NHC(O))-1-methyl-6-nBu-2-oxo-1,2-dihydropyridine | (R&S) cHept | Bn | 172 | |
| 48 | 2-methylquinolin-?-yl | (dia A) cPent | R-Gly | | 0.37 CH₂Cl₂/CH₃OH 100:10 |

TABLE 1-continued

| Ex. No. | A | R¹ | R² | M.p. (° C.) | R_f |
|---|---|---|---|---|---|
| 49 | 2-methylquinoline | (dia B) cPent | R-Gly | | 0.37 CH$_2$Cl$_2$/CH$_3$OH 100:10 |

What is claimed is:

1. A heterocyclically substituted phenylglycinolamide of the formula (I)

$$A-H_2C-\text{(phenyl)}-CO-NHR^2$$
$$\qquad\qquad\qquad\quad R^1$$

in which

A represents a radical of the formula in which

R⁶ and R⁷ are identical or different and denote hydrogen, phenyl, halogen, formyl, carboxyl, straight-chain or branched alkoxycarbonyl having up to 4 carbon atoms or straight-chain or branched alkyl having up to 4 carbon atoms, which is optionally substituted by hydroxyl, R¹ represents cycloalkyl having 3 to 8 carbon atoms, or represents straight-chain or branched alkyl having up to 10 carbon atoms, R² represents a radical of the formula $$-\underset{R^{13}}{\overset{\phantom{|}}{\text{CH}}}-R^{14},$$

in which

R¹³ is hydrogen or a radical of the formula CH$_2$—OH,

R¹⁴ is phenyl which is optionally substituted up to 3 times identically or differently by hydroxyl, halogen or straight-chain or branched alkyl having up to 5 carbon atoms, or a salt thereof.

2. A heterocyclically substituted phenylglycinolamide of the formula according to claim 1 in which A represents a radical of the formula in which R³, R⁴, R⁶ and R⁷ are identical or different and denote hydrogen, phenyl, fluorine, chlorine, bromine, formyl, straight-chain or branched alkoxycarbonyl having up to 3 carbon atoms or straight-chain or branched alkyl having up to 3 carbon atoms, which is optionally substituted by hydroxyl, R¹ represents cyclopropyl, cyclobutyl, cyclopentyl, cyclohexyl or cycloheptyl, or represents straight-chain or branched alkyl having up to 8 carbon atoms, R³ represents a radical of the formula $$-\underset{R^{13}}{\overset{\phantom{|}}{\text{CH}}}-R^{14},$$

in which

R¹³ denotes hydrogen or a radical of the formula CH$_2$—OH,

R¹⁴ denotes phenyl which is optionally substituted up to 2 times identically or differently by hydroxyl, fluorine, chlorine, bromine or straight-chain or branched alkyl having up to 3 carbon atoms, or a salt thereof.

3. A heterocyclically substituted phenylglycinolamide of the formula according to claim 1 in which A represents a radical of the formula in which R³, R⁴, R⁶ and R⁷ are identical or different and denote hydrogen, phenyl, chlorine, formyl, methoxycarbonyl, ethoxycarbonyl or methyl or ethyl, which is optionally substituted by hydroxyl, or a salt thereof.

4. A composition for the treatment of atherosclerosis comprising an amount effective therefore of a compound or salt thereof according to claim 1 and a pharmacologically acceptable diluent.

5. A method of treating atherosclerosis in a patient in need thereof which comprises administering to such patient an amount effective therefore of a compound or salt thereof according to claim 1.

6. The compound, according to claim 1, which has the formula

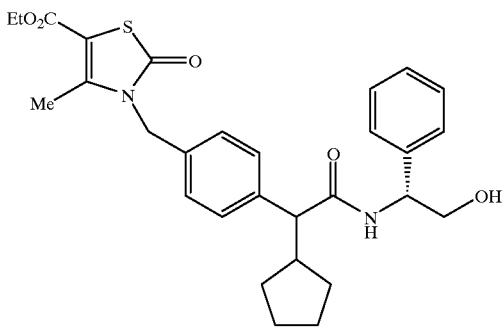

or a salt thereof.

7. The compound, according to claim 1, which has the formula

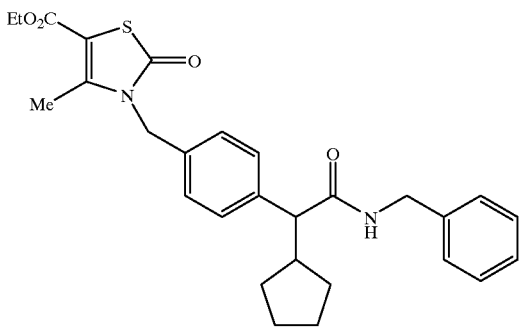

or a salt thereof.

8. The compound, according to claim 1, which has the formula

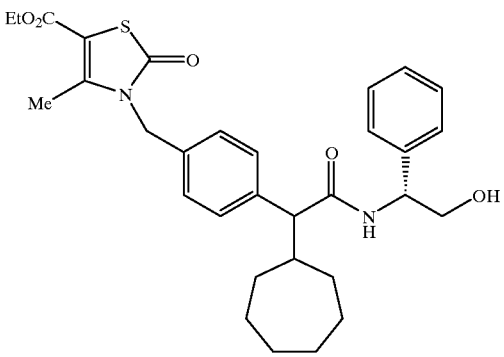

or a salt thereof.

9. The compound, according to claim 1, which has the formula

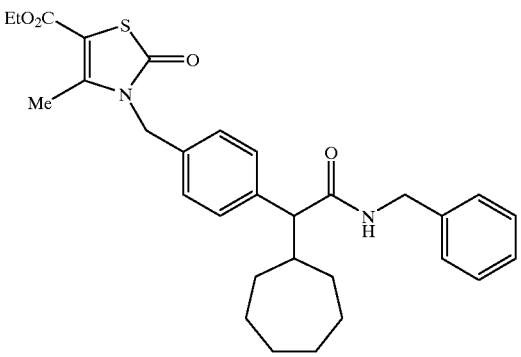

or a salt thereof.